United States Patent
Ochs et al.

(10) Patent No.: US 6,358,906 B1
(45) Date of Patent: Mar. 19, 2002

(54) CONCENTRATED LIQUID ACCUMULATIONS COMPRISING A MICROBICIDALLY ACTIVE INGREDIENT

(75) Inventors: Dietmar Ochs, Schopfheim (DE); Marcel Schnyder, Birsfelden (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/194,801

(22) PCT Filed: May 22, 1997

(86) PCT No.: PCT/EP97/02605

§ 371 Date: Dec. 2, 1998

§ 102(e) Date: Dec. 2, 1998

(87) PCT Pub. No.: WO97/46218

PCT Pub. Date: Dec. 11, 1997

(30) Foreign Application Priority Data

Jun. 4, 1996 (CH) ................................. 1403/96

(51) Int. Cl.$^7$ ................................. C11D 3/48
(52) U.S. Cl. ............... 510/382; 510/130; 510/131; 510/383; 510/488; 510/491; 510/498; 510/505
(58) Field of Search ................ 510/130, 131, 510/276, 492, 488, 491, 498, 499, 505, 382, 383

(56) References Cited

U.S. PATENT DOCUMENTS

| | | | |
|---|---|---|---|
| 3,800,048 A | * 3/1974 | Model et al. | 424/304 |
| 4,282,110 A | * 8/1981 | Koike | 252/107 |
| 4,761,247 A | 8/1988 | Rei et al. | 252/364 |
| 5,102,657 A | 4/1992 | Rei et al. | 514/504 |
| 5,234,832 A | * 8/1993 | Disch et al. | 435/264 |
| 5,374,378 A | 12/1994 | Lorentzen et al. | 252/380 |
| 5,403,864 A | 4/1995 | Bruch et al. | 514/721 |
| 5,589,448 A | * 12/1996 | Koerner et al. | 510/284 |

FOREIGN PATENT DOCUMENTS

| | | |
|---|---|---|
| CH | 604523 | 9/1978 |
| EP | 206987 | 12/1986 |
| EP | 0259249 | 7/1987 |
| EP | 0364159 | 4/1990 |
| EP | 0553628 | 8/1993 |
| EP | 0640285 | 3/1995 |
| EP | 0281398 | 9/1998 |
| GB | 1353681 | 5/1974 |
| GB | 2203339 | 10/1988 |
| WO | 93/07250 | 4/1993 |
| WO | 96/06152 | 2/1996 |
| WO | 97/46218 | 12/1997 |

* cited by examiner

Primary Examiner—Bruce H. Hess
Assistant Examiner—Dawn Garrett
(74) Attorney, Agent, or Firm—Kevin T. Mansfield

(57) ABSTRACT

There are described concentrated liquid formulations (a) comprising ($a_1$) 1 to 80% by weight of a microbicidally active ingredient, ($a_2$) 20 to 99% by weight of a mono- or dihydric alcohol or mixtures thereof, and concentrated liquid formulations (b) comprising ($b_1$) 5.1 to 30% by weight of microbicidally active ingredient, ($b_2$) 0 to 80% by weight of sulfonate, ($b_3$) 1 to 60% by weight of a $C_1$–$C_{11}$ monocarboxylic acid or of a $C_3$–$C_{12}$ di- or -polycarboxylic acid;

($b_4$) 0 to 90% by weight of a mono- or dihydric alcohol or mixtures thereof, and water to 100%, it always being necessary for one of the components ($b_2$) or ($b_4$) to be present.

The formulations according to the invention are used as microbicidally active ingredient in cosmetic products, household articles or hand disinfectants, as preservatives in household articles and cosmetic products and as disinfectant and decontamination agent for textile fibre materials or the skin and hard surfaces.

13 Claims, No Drawings

CONCENTRATED LIQUID ACCUMULATIONS COMPRISING A MICROBICIDALLY ACTIVE INGREDIENT

The present invention relates to liquid formulations comprising microbicidally active ingredients and to the use of these formulations as microbicidally active ingredient in cosmetic products, household articles or hand disinfectants and to the use as preservatives in household articles and cosmetic products.

The present invention relates to concentrated liquid formulations (a) comprising ($a_1$) 1 to 80% by weight of a microbicidally active ingredient, ($a_2$) 20 to 99% by weight of a mono- or dihydric alcohol or mixtures thereof, and concentrated liquid formulations (b) comprising ($b_1$) 5.1 to 30% by weight of a microbicidally active ingredient, ($b_2$) 0 to 80% by weight of a sulfonate, ($b_3$) 1 to 60% by weight of a $C_1$–$C_{11}$ monocarboxylic acid or of a $C_3$–$C_{12}$ di- or -polycarboxylic acid;

($b_4$) 0 to 90% by weight of a mono- or dihydric alcohol or mixtures thereof, and water to 100%, it always being necessary for one of the components ($b_2$) or ($b_4$) to be present.

The liquid formulation (a) preferably comprises ($a_1$) 20 to 70% by weight of a microbicidally active ingredient and ($a_2$) 30 to 80% by weight of a mono- or dihydric alcohol or mixtures thereof.

Formulation (b) prefer ably comprises ($b_1$) 10 to 30% by weight of a microbicidally active ingredient, ($b_2$) 0 to 80% by weight of a sulfonate, ($b_3$) 1 to 60% by weight of a $C_1$–$C_{11}$ monocarboxylic acid or of a $C_3$–$C_{12}$ di- or -polycarboxylic acid;

($b_4$) 0 to 90% by weight of a mono- or dihydric alcohol or mixtures thereof, and water to 100%.

Component ($a_1$) or ($b_1$) is, in particular, 2-hydroxydiphenyl ether, of the formula

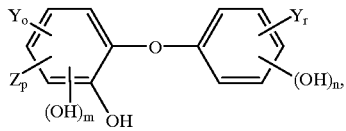

(1)

in which

Y is chlorine or bromine,

Z is $SO_2H$, $NO_2$ or $C_1$–$C_4$ alkyl, r is 0 to 3, o is 0 to 3, p is 0 or 1, m is 0 or 1 and n is 0 or 1.

Especially interesting compounds of the formula (1) are those in which

Y is chlorine or bromine, m is 0, n is 0 or 1, o is 1 or 2, r is 1 or 2 and p is 0.

Very especially interesting compounds of the formula (1) are those in which

Y is chlorine, m is 0, n is 0, o is 1, r is 2 and p is 0.

Very especially preferred is the compound of the formula

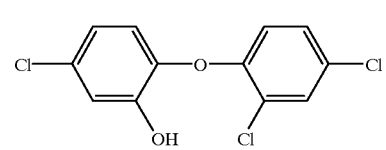

(2)

Other suitable microbicidally active ingredients which correspond to component ($a_1$) or ($b_1$) are phenol derivatives, diphenyl compounds, benzyl alcohols, chlorhexidine, $C_{12}$–$C_{14}$ alkylbetaines and $C_8$–$C_{18}$ fatty acid amido alkylbetaines, amphoteric surfactants, trihalocarbanilides and quaternary ammonium salts.

The phenol derivatives are preferably compounds of the formula

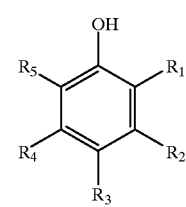

(3)

in which $R_1$ is hydrogen, hydroxyl, $C_1$–$C_4$ alkyl, chlorine, nitro, phenyl or benzyl, $R_2$ is hydrogen, hydroxyl, $C_1$–$C_6$ alkyl or halogen, $R_3$ is hydrogen, $C_1$–$C_6$ alkyl, hydroxyl, chlorine, nitro or a sulfur in the form of its alkali metal salts or ammonium salts, $R_4$ is hydrogen or methyl and $R_5$ is hydrogen or nitro.

Halogen is bromine or, preferably, chlorine.

Examples of such compounds are chlorophenols (o-, m-, p-), 2,4-dichlorophenol, p-nitrophenol, picric acid, xylenol, p-chloro-m-xylenol, cresols (o-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol and 4-phenolsulfonic acid.

The diphenyl compounds are preferably compounds of the formula

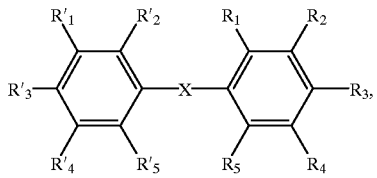

(4)

in which

X is sulfur or the methylene group, $R_1$ and $R'_1$ are hydroxyl and $R_2$, $R'_2$, $R_3$, $R'_3$, $R_4$, $R'_4$, $R_5$ and $R'_5$ independently of one another, are hydrogen or halogen.

Examples of compounds of the formula (4) are hexachlorophene, tetrachlorophene, dichlorophene, 2,3-dihydroxy-5,5'-dichlorodiphenyl sulfide, 2,2'-dihydroxy-3,3',5,5'-tetrachlorodiphenyl sulfide, 2,2'-dihydroxy-3,3',5,5',6,6'-hexachlorodiphenyl sulfide and 3,3'-dibromo-5,5'-dichloro-2,2'-dihydroxydiphenylamine.

The benzyl alcohols are preferably those of the formula

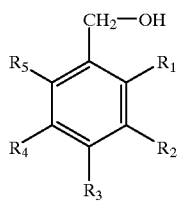

(5)

in which $R_1$, $R_2$, $R_3$, $R_4$ and $R_5$, independently of one another, are hydrogen or chlorine.

Examples of compounds of the formula (5) are benzyl alcohol, 2,4-, 3,5- or 2,6-dichlorobenzyl alcohol and trichlorobenzyl alcohol.

Chlorhexidine can be employed as such or in the form of its salt with organic and inorganic acids.

An example which may be mentioned of $C_8$–$C_{18}$ fatty acid amidoalkylbetaine is coconut fatty add $C_8$–$C_{18}$ amidopropylbetaine.

Examples of suitable amphoteric surfactants are $C_{12}$ alkylamino-, $C_1$–$C_3$ alkanecarboxylic acids, for example alkylaminoacetic acids or alkylaminopropionic acids.

Trihalocarbanilides are, in particular, those of the formula

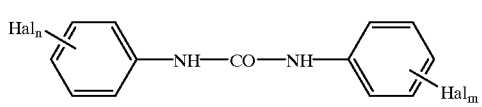

(6)

in which

Hal is chlorine or bromine, n and m are 1 or 2 and n+m are 3.

The quaternary ammonium salts are, in particular, those of the formula

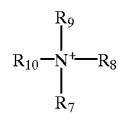

(7)

in which $R_7$, $R_8$, and $R_9$ and $R_{10}$, independently of one another, are $C_1$–$C_{18}$ alkyl, $C_1$–$C_{18}$ alkoxy or phenyl-$C_1$–$C_5$ alkyl and Hal is chlorine or bromine.

Very especially preferred is the compound of the formula

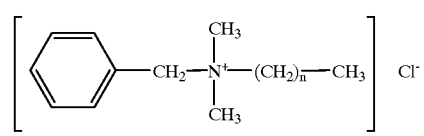

(8)

in which n is a number from 7 to 17.

Monohydic alcohols corresponding to component ($a_2$) or ($b_4$) are linear or branched $C_2$–$C_{18}$ alcohols, for example ethanol, n-propanol, isopropanol, butanol, lauryl alcohol, caryl alcohol, 2-ethylhexanol, 1,1,3,3-tetramethylbutanol, octan-2-ol, isononyl alcohol, trimethylhexanol, trimethylnonyl alcohol, decanol, $C_9$–$C_{11}$ oxo alcohol, tridecyl alcohol, isotridecyl alcohol or linear primary alcohols (®Alfol types) having 8 to 18 carbon atoms. Some representatives of these Alfol types are ®Alfol (8-10), ®Alfol (9-11), ®Alfol (10-14), ®Alfol (12-13) or ®Alfol (16-18).

Other substances which are preferably employed in the liquid formulations according to the invention are monohydric alcohols of the general formula

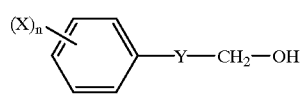

(9)

in which

X is a halogen atom

Y is a radical of the formula —O—$(CH_2)_m$— or —$CH_2$— or a direct bond;

n is 0 to 5; and m is 1 to 3.

Preferred compounds of the formula (9) are those in which

Y is —O—$(CH_2)_m$— and n=0.

If dihydric alcohols are employed as component ($a_2$), these have, in particular, 2 to 6 carbon atoms in the alkyl moiety, for example ethylene glycol, 1,2- or 1,3-propanediol, 1,3-, 1,4- or 2,3-butanediol, 1,5-pentanediol and 1,6-hexanediol. 1,2-Propanediol (propylene glycol) is preferred.

Suitable sulfonates (component ($b_2$)) are, in particular, their salts of terpenoids, or mono- or binuclear aromatic compounds, for example sulfonates of camphor, toluene, xylene, cumene or naphthol.

Suitable examples of component ($b_3$) as saturated or unsaturated $C_3$–$C_{12}$di- or polycarboxylic acids are malonic, succinic acid, glutaric acid, adipic acid, pimelic acid, suberic acid, azelaic acid and sebacic acid, undecane- and dodecanedicarboxylic acid, fumaric acid, maleic acid, tartaric acid and maleic acid, hydroxyacetic acid (glycolic acid), á-hydroxypropionic acid (lactic acid), and citric and aconitic acid.

Examples of aliphatic saturated or unsaturated $C_1$–$C_{11}$monocarboxylic acids are acetic acid, propionic acid, caproic acid, capric acid and undecylenoic acid.

Other suitable substances are aminocarboxylic acids, such as ethylenediaminetetraacetic acid, hydroxyethylethylenediaminetetraacetic acid and nitrilotriacetic acid; cycloaliphatic carboxylic acids, such as camphoric acid; aromatic carboxylic acids, such as benzoic acid, phenylacetic acid, phenoxyacetic acid and zimanic acid, 2-, 3- and 4-hydroxybenzoic acid, anilic acid, and o-, m- and p-chlorophenylacetic acid and o-, m- and p-chlorophenoxyacetic acid; alkali metal salts and amine salts of inorganic acids, such as the sodium salts, potassium salts and amine($R_1R_2R_3$) salts of hydrochloric acid, sulfuric acid, phosphoric acid, $C_1$–$C_{10}$alkylphosphoric acid and boric acid, $R_1$, $R_2$ and $R_3$ having the abovementioned meanings; isethionic acid; tannic acid; and acid amides of the formula

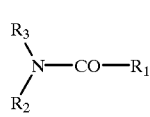

(10)

in which
$R_1$ is hydrogen or $C_1$–$C_{12}$alkyl and
$R_2$ and $R_3$ independently of one another are hydrogen, $C_1$–$C_{12}$alkyl, $C_2$–$C_{12}$alkenyl,
$C_1$–$C_{12}$hydroxyalkenyl, $C_2$–$C_{12}$hydroxyalkyl; or a polyglycol ether chain having 1 to 30 groups —$CH_2$—$CH_2$—O— or —$CHY_1$—$CHY_2$—O—, where
$Y_1$ or $Y_2$ is one hydrogen radical, the other being methyl, for example N-methylacetamide.

All carboxylic acids corresponding to component ($b_3$) which are employed in accordance with the invention can also preferably be employed in the form of their water-soluble alkali metal salts or ammonium salts.

Preferred liquid formulations (a) according to the invention comprise
($a_1$) 20 to 70, preferably 30 to 60, % by weight of a microbicidally active ingredient of the formula (1) and
($a_2$) 30 to 80, preferably 40 to 70, % by weight of a mono- or dihydric alcohol or mixtures thereof.

Very especially preferred are formulations which comprise, as component ($a_2$), the compound of the formula (9) as monohydric alcohol, and/or a dihydric alcohol which has 2 to 6 carbon atoms in the alkyl moiety.

Formulations which are preferably employed from amongst the above are formulations which comprise either a monohydric alcohol or a dihydric alcohol. In particular, a suitable monohydric alcohol is phenoxyethanol and a suitable dihydric alcohol 1,2-propanediol.

Preferred liquid formulations (b) comprise
($b_1$) 10 to 30, preferably 15 to 25, % by weight of a microbicidally active ingredient of the formula (1), ($b_2$) 0 to 80, preferably 10 to 70, % by weight of a sulfonate,
($b_3$) 1 to 60, preferably 10 to 50, % by weight of a $C_1$–$C_{11}$monocarboxylic acid or of a $C_3$–$C_{12}$di- or -polycarboxylic acid; and
($b_4$) 0 to 90, preferably 5 to 75, % by weight of a mono- or dihydric alcohol, and water to 100%, it always being necessary for one of components ($b_2$) or ($b_4$) to be present.

Very especially preferred liquid formulations (b) are those which comprise cumenesulfonate as component ($b_2$), a hydroxyacid as component ($b_3$) and a dihydric alcohol having 2 to 6 carbon atoms in the alkyl moiety as component ($b_4$).

Mainly of interest are liquid formulations (b) which comprise ($b_1$) 105 to 25% by weight of a microbicidally active ingredient of the formula (1),
($b_2$) 10 to 70% by weight of cumenesulfonate,
($b_3$) 10 to 50% by weight of lactic acid,
($b_4$) 5 to 75% by weight of 1,2-propanediol and
water to 100%.

The liquid formulations according to the invention are used as active ingredient in cosmetic products, for example deodorants, cleansers, lotions/creams, in household articles, for example as an additive in washing-up liquids, liquid household detergents; as an additive in dental care products, for example in mouthwashs or toothpastes, or as an antimicrobially active ingredient for hard and soft surfaces, for example polymers, paper, textiles and, in particular, the human skin.

The liquid formulations according to the invention are furthermore also suitable as preservatives for cosmetic products and household articles.

They are also used as disinfectants for textile fibre materials.

Liquid formulations according to the invention are prepared by dissolving component ($a_1$) or ($b_1$) in component ($a_2$) or ($b_4$), adding the components ($b_2$) and ($b_3$) to the resulting solution, with stirring, making up the resulting solution with deionized water to 90 to 95% of the final volume, if appropriate adjusting the pH with a cosmetically acceptable base, for example mono- or diethanolamine, and making up the mixture with deionized water to an end volume of 100%.

The dissolved microbicidally active ingredient can be incorporated into cosmetic products and household articles in a trouble free manner. The active ingredient, which is pulverulent per se, is offered to the user in dissolved form. Time-consuming predissolving in suitable solvents while supplying heat is no longer required.

Moreover, the liquid formulations according to the invention are distinguished by a synergistic antimicrobial action (see Example 15) and good storage stability.

The examples which follow illustrate the preparation of the liquid formulations according to the invention. Parts are parts by weight.

PREPARATION EXAMPLES FOR CONCENTRATED LIQUID FORMULATIONS

Example 1

| | |
|---|---|
| 60 Parts | of the compound of the formula (101) 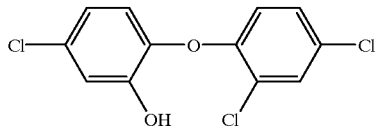 |
| | are introduced into a vessel. |
| 40 Parts | of 1,2-propanediol |
| | are added and the mixture is stirred at 50 to 60° C. at medium setting until the compound of the formula (101) is dissolved completely |

Example 2

| | |
|---|---|
| 30 Parts | of the compound of the formula (101) 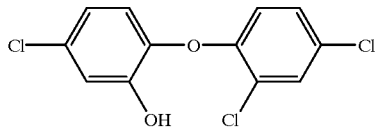 |
| | are introduced into a vessel. |
| 70 Parts | of 2-phenoxyethanol |
| | are added and the mixture is stirred at 50 to 60° C. at medium setting until the compound of the formula (101) is dissolved completely. |

Example 3

| | |
|---|---|
| 6 Parts | of the compound of the formula (101) and |
| 20 Parts | of 1,2-propanediol |
| | are weighed into a vessel and stirred at 50–60° C. at medium setting until a clear solution forms. Then, |
| 30 Parts | of citric acid, |
| 35 Parts | of sodium xylenesulfonate and |
| 4 Parts | of deionized water are added in the above sequence and stirring is continued until all constituents are dissolved. The pH of the mixture is brought to 3 to 4 by adding ethanolamine and the mixture is made up to 100 parts with deionized water. |

Example 4

| | |
|---|---|
| 15 Parts | of the compound of the formula (101) and |
| 10 Parts | of ethanol |
| | are weighed into a vessel and stirred at room temperature until a clear solution forms. Then, |
| 35 Parts | of undecylenoic acid |
| 20 Parts | of sodium xylenesulfonate and |
| 10 Parts | of deionized water |
| | are added in the above sequence and stirring is continued until all constituents are dissolved. The pH of the mixture is brought to 3 to 4 by adding ethanolamine and the mixture is made up to 100 parts with deionized water. |

Example 5

| | |
|---|---|
| 10 Parts | of the compound of the formula (101) and |
| 5 Parts | of 1,2-propanediol |
| | are weighed into a vessel and stirred at room temperature. |
| 30 Parts | of tartaric acid are added. The pH is then brought to 3 to 4 by adding ethanolamine. |
| 30 Parts | of sodium cumenesulfonate and |
| 10 Parts | of deionized water |
| | are added in the above sequence and stirring is continued until all constituents are dissolved. The mixture is made up to 100 parts with deionized water. |

Example 6

| | |
|---|---|
| 10 Parts | of the compound of the formula (101) and |
| 5 Parts | of 1,2-propanediol |
| | are weighed into a vessel and stirred at room temperature. |
| 40 Parts | of lactic acid |
| | are added. The pH is then brought to 3 to 4 by adding ethanolamine. |
| 30 Parts | of sodium cumenesulfonate and |
| 10 Parts | of deionized water |
| | are added in the above sequence and stirring is continued until all constituents are dissolved. The mixture is made up to 100 parts with deionized water. |

Example 7

10 Parts of the compound of the formula (101) and
10 Parts of 1,3-butanediol
are weighed into a vessel and stirred at room temperature until a clear solution forms. Then,
30 Parts of tartaric acid,
30 Parts of sodium cumenesulfonate and
10 Parts of deionized water
are added in the above sequence and stirring is continued until all constituents are dissolved. The pH of the mixture is brought to 3 to 4 by adding ethanolamine. The mixture is made up to 100 parts with deionized water.

Examples 8 to 13

Other Liquid Formulations with Alternative Microbicidally Active Ingredients

Example 8

10 Parts of benzyl alcohol and
5 Parts of propylene glycol are weighed into a vessel and stirred at room temperature. Then,
40 Parts of lactic acid,
30 Parts of sodium cumenesulfonate and
10 Parts of deionized water are added in the above sequence and stirring is continued until all constituents are dissolved. The pH of the mixture is brought to 5.5 by adding monoethanolamine, and the mixture is made up to 100 parts with deionized water.

Example 9

10 Parts of 2,4-dichlorobenzyl alcohol and
5 Parts of propylene glycol
are weighed into a vessel and stirred at room temperature until a clear solution forms. Then,
40 Parts of lactic acid,
30 Parts of sodium cumenesulfonate and
10 Parts of deionized water
are added in the above sequence and stirring is continued until all constituents are dissolved. The pH of the mixture is brought to 5.5 by adding monoethanolamine, and the mixture is made up to 100 parts with deionized water.

Example 10

10 Parts of p-chloro-m-xylenol,
5 Parts of propylene glycol and
30 Parts of sodium cumenesulfonate are weighed into a vessel and stirred at room temperature until a clear solution forms. Then,
40 Parts of lactic acid and
10 Parts of deionized water
are added in the above sequence and stirring is continued until all constituents are dissolved. The pH of the mixture is brought to 5.5 by adding ethanolamine, and the mixture is made up to 100 parts with deionized water.

Example 11

10 Parts of o-phenylphenol und
5 Parts of propylene glycol
are weighed into a vessel and stirred at 50–60° C. at medium setting until a clear solution forms. Then,
40 Parts of lactic acid,
30 Parts of sodium cumenesulfonate and
10 Parts of deionized water are added in the above sequence and stirring is continued until all constituents are dissolved. The pH of the mixture is brought to 5.5 by adding monoethanolamine, and the mixture is made up to 100 parts with deionized water.

Example 12

10 Parts of p-chloro-m-cresol and
5 Parts of propylene glycol
are weighed into a vessel and stirred at 50–60° C. at medium setting until a clear solution forms. Then,
40 Parts of lactic acid,
30 Parts of sodium cumenesulfonate and
10 Parts of deionized water
are added in the above sequence and stirring is continued until all constituents are dissolved. The pH of the mixture is brought to 5.5 by adding ethanolamine, and the mixture is made up to 100 parts with deionized water.

Example 13

10 Parts of benzalkonium chloride and
5 Parts of propylene glycol
are weighed into a vessel and stirred at room temperature until a clear solution forms. Then,
40 Parts of lactic acid,
30 Parts of sodium cumenesulfonate and
10 Parts of deionized water
are added in the above sequence and stirring is continued until all constituents are dissolved. The pH of the mixture is brought to 5.5 by adding monoethanolamine, and the mixture is made up to 100 parts with deionized water.

Example 14

Detection of the Microbicidal Activity in the Suspension Test

| | |
|---|---|
| Test microorganisms | *Staphylococcus aureus* ATCC 9144<br>*Enterococcus faecium* ATCC 10541<br>*Escherichia coli* ATCC 10536<br>*Pseudomonas aeruginosa* CIP A-22<br>*Candida albicans* ATCC 10231 |
| Nutrient media: | Casein soy flour peptone broth for growing the inoculum<br>Casein soy flour peptone agar with 3% polyoxyethylene(20) sorbitanmonooleate; 0.3% lecithin; 0.1% L-histidine |
| Dilution medium: | Trypticase soy flour peptone broth with 10% polyoxyethylene(20) sorbitanmonooleate, 3% lecithin; 0.1% L-histidine and 0.5% sodium thiosulfate. | a. Use of the Formulation of Example 6 as Disinfectant

These tests show that the liquid formulations according to the invention have a very potent microbicidal activity, even at low concentrations. These properties are important for disinfectants in general, but in particular for the disinfection of textiles.

Procedure:

0.1 ml of the formulation of Example 6 is diluted with 8.9 ml of water and the dilution is subsequently treated with 1 ml of a 1:10 dilution of a culture of the test bacteria which is incubated for 16 to 24 hours at 37° C. (=1% of the formulation of Example 6).

The concentration of the test organisms in the batch is $10^8$ microorganisms/ml. The batch is mixed thoroughly and subsequently incubated for 5 minutes at room temperature with gentle stirring.

After 5 minutes, 1 ml of the batch is removed and the live bacterial count is determined. To this end, dilutions are performed in dilution medium, and 0.1 ml each of these dilutions are plated onto agar media.

The live bacterial count is determined after the plates have been incubated for 24 to 48 hours at 37° C. by counting the colonies taking into consideration the dilution factor.

The test results are shown in Table 1.

TABLE 1

| | Reduction in bacterial count after 5 minutes (log) | | | |
|---|---|---|---|---|
| Batch | S. aureus ATCC 9144 | Ent. faecium ATCC 10541 | E. coli ATCC 10536 | P. aeruginosa CIP A-22 |
| Water | 0 | 0 | 0 | 0 |
| 1% Formulation 6 | >$10^5$ | >$10^5$ | >$10^5$ | >$10^5$ |

The tested formulation of Example 6 shows a reduction of all test microorganisms by at least 5 powers of ten after as little as 5 minutes in the suspension test.

b. Liquid Soap with a Concentrated Formulation Comprising 2,4,4'-trichloro-2'-hydroxydiphenyl Ether The tests of Examples 14b. and 14c. show that soap formulations to which the liquid formulations according to the invention are added have a powerful microbicidal activity, which is required for use as a disinfectant or decontaminant for hands, but also for the microbicidal treatment of surfaces (surface disinfectants, antimicrobial dishwashing products, household detergents and the like).

Test formulation:

| 4% | of sodium lauryl sulfate |
| 10% | of formulation of Example 6 |
| to 100% | water |

The pH is brought to 5.5 using ethanolamine.
Procedure:

9 ml of the formulation are mixed with 1 ml of a 1:10 dilution of a bacterial suspension which has been incubated at 37° C. for 16 to 24 hours, and the mixture is subsequently incubated at room temperature with stirring.

After an incubation time of 30 seconds, 1 ml of the test batch is removed, diluted in dilution medium, and 0.1 ml each of the dilutions are plated onto agar media.

After the plates have been incubated for 24 to 48 hours at 37° C., the live microbial count is determined by counting the colonies taking into consideration the dilution factor.

The test results are shown in Table 2.

TABLE 2

| Test microorganism | Reduction of test microorganisms after 30 seconds (Log) |
|---|---|
| S. aureus ATCC 9144 | >5 |
| E. faecium ATCC 10541 | >5 |
| E. coli ATCC 10536 | >5 |
| P. aeruginosa CIP A-22 | >5 |
| S. marcescens ATCC 13880 | 2.2 |
| C. albicans ATCC 10231 | 2.4 |

The liquid soap shows a very powerful microbicidal activity against the microorganisms tested.

c. Liquid Soaps with Concentrated Formulations
Test formulations:
Soaps of the following compositions are tested:

| 4% | of sodium lauryl sulfate, |
| 10% | of concentrated formulation of Examples 9 to 14, |
| to 100% | water |

The pH is brought to 5.5 using monoethanolamine.
Procedure:

9 ml of the formulation are mixed with 1 ml of a 1:10 dilution of a bacterial suspension which has been incubated at 37° C. for 16 to 24 hours, and the mixture is subsequently incubated at room temperature with stirring.

After an incubation time of 1 minute, 1 ml of the test batch is removed, diluted in dilution medium, and 0.1 ml each of the dilutions are plated onto agar media.

After the plates have been incubated for 24 to 48 hours at 37° C., the. live microbial count is determined by counting the colonies taking into consideration the dilution factor. test results are shown in Table 3:

TABLE 3

| Test soap with concentrated formulation of Example | Reduction of test microorganisms after 1 minute (log) P. aeruginosa CIP A-22 |
|---|---|
| 9 | >5 |
| 10 | >5 |
| 11 | >5 |
| 12 | >5 |
| 13 | >5 |
| 14 | >5 |
| Placebo | 0.9 |

All formulations tested show a potent bactericidal activity.

Example 15

Preservative Stress Tests with Liquid Soaps

Repetitive preservative stress tests (triple stress) demonstrate that the concentrates are highly suitable for the preservation of cosmetics and household articles.
Soap formulation:

| 6% | of sodium laureth-2 sulfate, |
| to 100% | water |

The pH is brought to 5.5 with monoethanolamine.

The soap formulation is preserved with the following concentrated formulations:

A: 3% of the formulation of Example 7
B: 1% of the formulation of Example 2

| | |
|---|---|
| Test microorganisms | *Staphylococcus aureus* ATCC 9144
*Escherichia coli* ATCC 10536
*Enterobacter gergoviae* ATCC 33028
*Klebsiella oxytoca* DSM 30106
*Pseudomonas aeruginosa* CIP A-22
*Pseudomonas fluorescens* ATCC 17397
*Candida albicans* ATCC 10231
*Aspergillus niger* ATCC 6275 |
| Nutrient media | Casein soy flour peptone agar with 3% polyoxyethylene(20) sorbitanmonooleate; 0.3% lecithin; 0.1% L-histidin for bacteria and yeasts |
| Dilution medium: | Trypticase soy flour peptone broth with 10% polyoxyethylene(20)sorbitanmonooleate; 3% lecithin; 0.1% L-histidine and 0.5% sodium thiosulfate. |

Procedure:

20 g of the soap formulation in question are inoculated with 0.2 ml of a microorganism suspension in such a way that the resulting microbial stress of the product is $10^5$ to $10^6$ microorganisms/g of product.

In order to determine the total microbial count at a particular point in time, 1 g of material is removed, and a dilution series is established in dilution medium. The total microbial count is determined by plating 0.1 ml of the dilutions onto agar media after incubation at 37° C. for 24 hours (bacteria and yeasts) or incubation at 28° C. for 5 days (Aspergillus).

The total bacterial count in the product is determined after inoculation and also after 1 and 2 weeks. After 2 and 4 weeks, the product is again inoculated in the same manner with test microorganisms, and the total microbial counts are determined after a further 1 and 2 weeks in each case.

The test results are shown in Table 4:

TABLE 4

| | Preservation | | |
|---|---|---|---|
| Test microorganisms | A | B | Unpreserved |
| *S. aureus* ATCC 9144 | +/+/+ | +/+/+ | −/−/− |
| *E. coli* ATCC 10536 | +/+/+ | +/+/+ | −/−/− |
| *Ent. gergoviae* ATCC 33028 | +/+/+ | +/+/+ | −/−/− |
| *Ps. aeruginosa* CIP A-22 | +/+/+ | +/+/+ | −/−/− |
| *Ps. fluorescens* ATCC 17397 | +/+/+ | +/+/+ | −/−/− |
| *C. albicans* ATCC 10231 | +/+/+ | +/+/+ | −/−/− |
| *Aspergillus niger* ATCC 6275 | +/+/+ | +/+/+ | −/−/− |

+ = Reduction of total bacterial count of at least 99% in the course of 2 weeks after an inoculation.
− = Reduction of total microbial count of less 99% in the course of 2 weeks after an inoculation.

Example 16

Preparation of a Syndet (detergent formulation)

15.7% of alkylarylsulfonate
3.7% of fatty alcohol sulfonate
2.7% of fatty acid monoethanolamide
39% of tripolyphosphate
4% of sodium silicate
2% of magnesium silicate
1% of carboxymethylcellulose
0.5% of EDTA
2% of the formulation of Example 2
4.7% of water Preparation:

The ingredients are stirred with equivalent amounts of water to a slurry. The resultant paste is dried at 50° C. and finally pressed through a sieve with a mesh diameter of 0.8 mm. Particles <0.3 mm are discarded.

Example 17

Preparation of a Dishwashing Product

7% of sodium lauryl sulfate
7% of sodium myreth sulfate
4% of lauryl glucoside
1% of cocamidopropylbetaine
1% of the formulation of Example 6
1% of sodium chloride
0.02% of dibromodicyanobutane
0.08% of phenoxyethanol
78.9% of water Preparation:

Sodium lauryl sulfate are mixed with sodium myreth sulfate and lauryl glucoside and solved in 30 parts of water. The formulation of Example 6 is added and homogenized. Cocamidopropylbetaine, sodium chloride, dibromodicyanobutane and phenoxyethanol are added. The pH is adjusted to 6.0 with citric acid. Water is added to give 100 parts.

Example 18

Preparation of a Disinfectant for Textiles

| | |
|---|---|
| 50% | of the formulation of Example 6 |
| 10% | of lauryl alcohol polyglycol ether |
| to 100% | of water |

The pH is brought to 5 with monoethanolamine.

Example 19

Preparation of a Hand Disinfectant

4% of
0.5% of hydroxyethylcellulose
3% of the formulation of Example 2
to 100% of water Preparation:

Sodium lauryl sulfate are dissolved in 20 parts of water, the formulation of Example 2 is added. Hydroxyethylcellulose is dissolved in 60 parts of water at 60° C., cooled down and added to the surfactant mixture. The pH is adjusted to 5.5 with monoethanolamine. Water is added to give 100 parts.

Example 20

Preparation of a Hand Disinfectant

| | |
|---|---|
| 4% | of sodium lauryl sulfate |
| 0.5% | of hydroxyethylcellulose |
| 10% | of the formulation of Example 7 |
| to 100% | of water |

The pH is brought to 5.5 with monoethanolamine
Preparation:
Sodium lauryl sulfate are dissolved in 20 parts of water, the formulation of Example 2 is added. Hydroxyethylcellulose is dissolved in 60 parts of water at 60° C., cooled down and added to the surfactant mixture. The pH is adjusted to 5.5 with monoethanolamine. Water is added to give 100 parts.

Example 21

Preparation of a Shower Gel

| | |
|---|---|
| 6% | of sodium laureth-2 sulfate |
| 3% | of cocamidopropylbetaine |
| 1.5% | of hydrolysed protein |
| 1.5% | of laureth-9 |
| 0.3% | of polyquaternium-7 |
| 1% | of the liquid formulation of Example 2 |
| 1.0% | of glycol distearate |
| 0.2% | of sodium chloride |
| to 100% | of water |

Preparation:
Glycol distearate is dissolved in sodium laureth-2 sulfate at 50° C. The remaining ingredients and 30 parts of water are added in succession and homogenized.

The pH is adjusted to 5.5 with monoethanolamine and water is added to give 100 parts.

Instead of 1% of the formulation of Example 2, it is also possible to employ 0.5–1.5% of the formulation of Example 1 or 1–10% of the formulation of Examples 3 to 12.

What is claimed is:

1. A concentrated liquid formulation (a) consisting essentially of
   ($a_1$) 20 to 70% by weight of a microbicidally active ingredient which is a 2-hydroxydiphenylether of formula

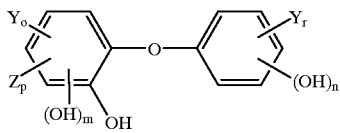

(1)

in which
   Y is chlorine or bromine,
   Z is $SO_2H$, $NO_2$ or $C_1$–$C_4$alkyl,
   r is 1 or 2,
   o is 1 or 2,
   p is 0,
   m is 0 and
   n is 0 or 1; and
   ($a_2$) 30 to 80% by weight of a mono- or dihydric alcohol or mixtures thereof, or,
a concentrated liquid formulation (b) consisting essentially of
   ($b_1$) 10 to 30% by weight of a microbicidally active ingredient which is a 2-hydroxydiphenylether of formula (1),
   ($b_2$) 0 to 80% by weight of a sulfonate,
   ($b_3$) 1 to 60% by weight of a $C_1$–$C_{11}$monocarboxylic acid or of a $C_3$–$C_{12}$di- or -polycarboxylic acid
   ($b_4$) 0 to 90% by weight of a mono- or dihydric alcohol or mixtures thereof, and water to 100%, wherein at least one of the optional components ($b_2$) or ($b_4$) is present in the formulation (b).

2. A liquid formulation according to claim 1, wherein component ($a_1$) or ($b_1$) has the formula

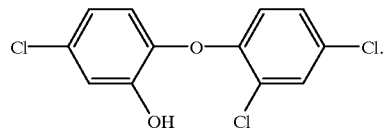

(2)

3. A liquid formulation according to claim 1, wherein component ($a_2$) or ($b_4$) represents monohydric linear or branched $C_2$–$C_{18}$alcohols.

4. A liquid formulation according to claim 1, wherein alcohols of the general formula

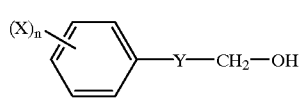

(9)

are employed, as component ($a_2$) or ($b_4$), in which
   X is a halogen atom,
   Y is a radical of the formula —O—$CH_2$— or —$CH_2$— or a direct bond; and
   n is 0 or an integer from 1 to 5.

5. A liquid formulation according to claim 1, wherein dihydric alcohols having 2 to 6 carbon atoms in the alkyl moiety are employed as component ($a_2$) or ($b_4$).

6. A liquid formulation according to claim 1,
   ($b_1$) 15 to 25% by weight of a microbicidally active ingredient of the formula (1);
   ($b_2$) 10 to 70% by weight of cumenesulfonate;
   ($b_3$) 10 to 50% by weight of lactic acid;
   ($b_4$) 5 to 75% by weight of 1,2-propanediol and water to 100%.

7. A cosmetic product which comprises an antimicrobially effective amount of a liquid formulation according to claim 1 as the antimicrobially active ingredient.

8. A household article which comprises an antimicrobially effective amount of a liquid formulation according to claim 1 as the antimicrobially active ingredient.

9. A method of preserving cosmetic products which comprises incorporating an antimicrobially effective amount of a liquid formulation according to claim 1 therein.

10. A method of preserving household articles which comprises contacting them with an antimicrobially effective amount of a liquid formulation according to claim 1.

11. A method according to claim 10 wherein the household article is a textile material.

12. A method of decontaminating hard and soft surfaces which comprises contacting them with an antimicrobially effective amount of a liquid formulation according to claim 1.

13. A method according to claim 12 wherein the surface is human skin.

* * * * *

UNITED STATES PATENT AND TRADEMARK OFFICE
CERTIFICATE OF CORRECTION

PATENT NO.    : 6,358,906 B1                                            Page 1 of 1
DATED         : March 19, 2002
INVENTOR(S)   : Dietmar Ochs et al.

It is certified that error appears in the above-identified patent and that said Letters Patent is hereby corrected as shown below:

<u>Title page,</u>
Item [54], the title should read:

-- [54] CONCENTRATED LIQUID FORMULATION COMPRISING A MICROBICIDALLY ACTIVE INGREDIENT --.

Signed and Sealed this

Tenth Day of September, 2002

Attest:

Attesting Officer

JAMES E. ROGAN
*Director of the United States Patent and Trademark Office*